United States Patent [19]
Silverman

[11] Patent Number: 4,728,637
[45] Date of Patent: Mar. 1, 1988

[54] COMPLEX OF MACROMOLECULES EXTRACTED FROM MESENCHYMAL CELLS FOR TREATING CHRONIC DEGENERATIVE DISEASE

[76] Inventor: Ralph Silverman, 7701 W. Arcadia, Morton Grove, Ill. 60053

[21] Appl. No.: 842,475

[22] Filed: Mar. 21, 1986

Related U.S. Application Data

[63] Continuation-in-part of Ser. No. 549,257, Nov. 4, 1983, abandoned.

[51] Int. Cl.[4] .................. A61K 37/10; A61K 37/02
[52] U.S. Cl. ............................................. 514/8; 514/2; 514/21; 514/801; 435/68; 435/240.21; 435/240.23; 435/240.25
[58] Field of Search .................... 435/240, 241; 514/2, 514/8, 21

[56] References Cited

PUBLICATIONS

Yamada et al.–Chem. Abst. vol. 101 (1984), p. 207 169m.
Baum et al.–Chem. Abst. vol. 88 (1978), p. 19630w.
Uchida et al.–Chem. Abst. vol. 91 (1979), p. 33533h.
Viljanto et al.–Chem. Abst. vol. 95 (1981), p. 40361m.

*Primary Examiner*—Sam Rosen
*Attorney, Agent, or Firm*—Laff, Whitesel, Conte & Saret

[57] ABSTRACT

This invention provides a pharmaceutical complex of macromolecules selected from the group consisting of animal and human mesenchymal cells and wherein the macromolecules are fibronectins and procollagens and are produced by the process comprising culturing mesenchymal cells in an appropriate medium to permit the cells to excrete macromolecules into the medium to provide a harvested medium and separating the desired macromolecules from the harvested medium. The complex is used to treat chronic degenerative diseases.

5 Claims, No Drawings

COMPLEX OF MACROMOLECULES EXTRACTED FROM MESENCHYMAL CELLS FOR TREATING CHRONIC DEGENERATIVE DISEASE

This is a continuation-in-part of my application Ser. No. 06/549,257 filed on Nov. 4, 1983, now abandoned.

This invention relates to a pharmaceutical complex for treating humans and animals with degenerative diseases. The complex comprises a mixture of macromolecules produced from human and animal cultured mesenchymal cells. The mesenchymal cell macromolecular complex consists of fibronectin and procollagen, with or without the macromolecules selected from proteoglycan, elastin, laminin and mixtures thereof. Whether or not proteoglycan, laminin or elastin are present depends on the particular mesenchymal cell culture used to prepare the complex of my invention.

The invention also relates to treating humans and animals with the mesenchymal macromolecular complex of fibronectin and procollagen, which may further include macromolecules selected from the group proteoglycan, laminin, elastin or mixtures thereof.

Chronic degenerative diseases are mainly treated with drugs and radiation treatments. Such treatment is foreign to the physiological system. The exact manner in which many of these treatments work upon the diseased state is unknown, and their use is based upon trial-and-error observations and studies on humans and animals.

The problem with drugs and/or radiation therapy is that they usually destroy or injure the healthy cells along with the diseased cells. Further, it is almost impossible to localize the treatment only to the diseased area. Thus, not only are healthy cells in the immediate area affected, but also those outside of the diseased area. By destroying or injuring these healthy cells, these treatments often lead to severe side effects including allergies and immunological breakdown. If the treatment comprises a patient's immune system, other life-threatening diseases such as viral or bacterial pneumonias can occur, and further treatments are undermined by the onset of these complications.

For the ease of further describing my invention, I will refer to my composition as PROFIPEL. It is to be understood that this covers those instances where the composition contains all five ingredients —fibronectins, procollagens, proteoglycans, laminins and elastins; four ingredients—fibronectins, procollagens, proteoglycans, and either elastins or laminins; three ingredients—fibronectins, procollagens and proteoglycans, or the two ingredients, fibronectins and procollagens.

The macromolecules extracted from cultured mesenchymal cells, the PROFIPEL, function with each other in consort and not individually. Therefore, they must not be considered as individual ingredients but must be considered as a complex of mesenchymal macromolecules.

The PROFIPEL is placed in a therapeutically useful form for administration to the ill animal or human and is particularly useful in treating chronic degenerative diseases which affect the epithelial tissue. These diseases cause abnormal cells with the abnormal or diseased cells being regenerated.

Accordingly, an object of this invention is to avoid the use of foreign agents such as drugs and radiation in the treatment of chronic degenerative diseases.

Another object of the invention is to provide a complex of mesenchymal macromolecules which promote redifferentiation of chronically diseased cells and tissue.

Still another object is to provide a complex which is specific for the particular type of tissue being treated.

My preferred embodiments of this invention will be described by use of macromolecules produced by human mesenchymal tissues underlying epithelial tissues. This, of course, is not intended to limit my invention to pharmaceuticals for humans. The same procedure and compositions are also intended for use on animals. In the case of animals the use of animal mesenchymal cells to produce the complex would be preferred.

The term "differentiate" is a well known term defining a cell in its most normal healthy state.

"Dedifferentiate" is a cell in an abnormal and diseased state which regenerates in an abnormal state. This is what is believed to occur with degenerative diseases such as sarcoma tumors, adenocarcinomas and the like.

"Redifferentiate" as used herein means that the diseased cells tend to regenerate toward their normal genetic potential.

"Chronic degenerative disease" is a pathological condition of the body of long duration and slow progression with deterioration or impairment of an organ or part in structure of the cells and substances of which they are a part.

The exact mechanism by which PROFIPEL acts on the diseased tissue is not known. However, it is believed that PROFIPEL tends to redifferentiate the diseased cells. That is, stop or slow down the diseased cells from generating in their abnormal state and thereby promote the natural generation of healthy cells. The complex of macromolecules are the fibronectins, procollagens, proteoglycans, laminins and elastins referred to as PROFIPEL. These macromolecules act in consort although their exact functions are not completely understood. In this invention, the therapeutic administration of PROFIPEL promotes the redifferentiation of the diseased cells and tissue.

The type of mesenchymal cells used to produce PROFIPEL can vary. Although it is not required, it is believed that for the treatment of a specific diseased tissue it would be best to prepare PROFIPEL from that type of mesenchymal tissue. For example, if the diseased tissue is lung tissue, then the PROFIPEL used to treat the disease is preferably collected from cultured lung mesenchymal cells.

By varying the type of mesenchymal cells (i.e., periodontal lung, liver, skin, etc.) for a specific diseased tissue, the components of the PROFIPEL complex will vary. For example, as stated above, proteoglycans laminins and elastins may not be present in certain complexes of PROFIPEL, whereas, fibronectins and procollagens will always be present. Further, the relative quantitative amounts and molecular weights of the various components of PROFIPEL may vary from site to site.

I obtain my PROFIPEL from the culture medium of various types of healthy normal mesenchymal cells in a similar manner. First, various healthy human mesenchymal tissues, usually specific in situ fibroblasts, are obtained from consenting human donors or from other sources such as The American Type Culture Collection of Rockville, Md., which has many types of available normal human fibroblasts frozen in liquid nitrogen.

The normal mesenchymal tissue obtained from human donors, is cut into small pieces and treated with the proteolytic enzyme trypsin. This yields a mixture of single cells or small clumps of cells. The cells are then collected by centrifugation. These cells are inoculated into a culture flask containing a suitable growth medium such as Eagles Minimum Essential Medium (MEM) plus 10% fetal calf serum (FCS) which has been filtered through a 0.22 micron millipore filter to eliminate its large molecular weight proteins or an appropriate serum free medium such as or a combination of mediums as hereinafter set forth. The invention is not intended to be limited by the particular medium used. The medium set forth herein are those known to me.

The flask containing the growth medium and the cells is incubated at 37° C. in an incubator having a 5% carbon dioxide atmosphere. The flask is incubated until the cell culture reaches confluence, which means that the culture covers the total bottom of the culture flask in a single layer. Usually, this occurs within 3 to 12 days.

The cells are next released from the flask by trypsin and EDTA, which are protein digesting agents. The released cells are then reinoculated into several culture flasks in order to expand the culture, and the above incubation step at 37° C. in a 5% carbon dioxide atmosphere is repeated. Preferably, a small portion of the released cells are frozen and stored in liquid nitrogen for future culture sources.

If frozen cells from the American Type Culture Collection are utilized, these cells are thawed and the culture is started in the same manner as described above.

The cell lines are further expanded by splitting confluent cultures and transferring the cultures to larger cultural vessels such as roller bottles or cultural appliances such as a Hollow Fiber Prefusion Reactor.

The cultured cells excrete their synthesized PROFIPEL macromolecules into the culture medium. These molecules are excreted into the medium in soluble form. The purpose of expanding the cell lines is to obtain as much culture medium as possible. The culture medium is then processed to isolate the soluble PROFIPEL molecules from the medium.

The medium should be processed and separated from the cell culture in one to four days after confluency is reached. The medium can be processed immediately after collection from the culture, or it can be frozen until processing is performed without any loss of protein activity of the soluble PROFIPEL molecules.

Processing and extraction of the PROFIPEL complex from the medium is accomplished by first centrifuging the medium for one half hour at 15,000 rpm. Centrifugation removes the cell fragments, and the clarified medium is then placed onto a chromatography column, i.e. G150 gel or G-25 gel chromatography column. The fractions of substrate are collected from the void volume of the column and pooled and these contain the PROFIPEL complex. This void volume of the column can be quantitatively measured by passing blue dextran through the empty column.

The initial protein fractions collected from the void volume are observed on a spectrophotometer at optical density of 280 U.V. The collected fractions are pooled, and these pooled fractions contain the soluble fibronectins, procollagens, proteoglycans, laminins and elastins. Only fractions made from one specific type of mesenchymal tissue are pooled. For example, fractions synthesized from lung mesenchymal tissue are only pooled with other fractions made from cultures of lung cells.

If desired, a further purification step is done by placing the pooled solute on a FPLC ion exchange chromatography system. Pharmacia Fast Protein, Polypeptide, liquid chromatography systems. This system purifies by ion exchange chromatography utilizing a rigid monodisperse matrix. The PROFIPEL proteins are purified in the ion exchange made of the FPLC by the difference of their isoelectric points.

The pooled fractions are then lyophilized (freeze-dried) to a powdered material by drying fractions in a frozen state under high vacuum. The pooled fractions can be placed in the final therapeutic ampules, flasks or other containers for the lyophilization procedure. In this way, the lyophilized powder can be reconstituted without further handling. For example, 10 cc of pooled fraction in a container could be lyophilized to approximately 2 mg of PROFIPEL. The lyophilized PROFIPEL can later be reconstituted in the same container with the amount of sterile saline needed for the selected dosage.

CULTURE MEDIUM 1

A culture medium was prepared using one liter of Eagles Minimum Essential Medium (MEM) plus glutamine, plus 10% Fetal Calf Serum (FCS) to which was added 1 ml Penicillin, 25 ml Streptomycin, 0.6 ml Genomycin, 0.5 ml Fungizone, 10 mls 10% Sodium Bicarbonate, 10 mls MEM Vitamins and 10 mls non-essential amino acids.

CULTURE MEDIUM 2

A serum free medium such as Medium 199 purchased from GIBCO which is fortified with Earle's salts, Triodothyromine, EGF, insulin, transferrin, cholesterol and thrombin.

CULTURE MEDIUM 3

A combination of mediums is used. The first to be used is a mixture of Medium 199, Earle's salts and the Fetal Calf Serum (FCS). This medium is used in the first step of all production. After confluence the medium is removed and the medium now used is medium 2 which does not contain FCS.

The above mediums are for illustrative purposes only and are not intended to limit my invention. Any appropriate medium may be used that would provide for the cell growth and permit the excretion of PROFIPEL molecules therein. With both mediums 1 and 3 the following cell growth was performed.

EXAMPLE 1

Frozen human foreskin fibroblasts, obtained from the Department of Microbiology, University of Illinois Medical Center, were thawed in a 16 ounce glass flask to which 20 mls of medium was added. The flask was placed into an incubator at 37° C. with a 5% carbon dioxide atmosphere and all subsequent incubations were at the same temperature and atmosphere.

The cells reached confluence in 6 days. The cells were transferred using sterile technique into a 32 ounce glass flask. This was accomplished by discarding the spent medium and adding to the flask 5 mls of 0.4% trypsin in 10% Versene (EDTA) for 45 seconds, which helps detach cells from the flask by digesting the attaching proteins. The trypsin-EDTA mixture was discarded and the small flask was washed repeatedly with 10 mls of medium with an electric pipette in order to release the cells into the 10 mls of medium. When all of the cells were released from the flask, the 10 mls of medium containing the cells were pipetted into a sterile 32 ounce flask containing 30 mls of medium, and returned to the incubator.

The cells reached confluence in 7 days and completely covered the bottom of the flask. The cells were again transferred by the above method and the released cells were divided in half and added to two 32 ounce flasks. The spent medium at this stage was saved and frozen. The culture was eventually expanded to fifty 32 ounce flasks and maintained at that level. Each flask contained 40 mls of medium and at each transfer, the spent medium was saved and stored in the freezer.

The PROFIPEL molecules are excreted into the medium by the fibroblasts and extracted from the stored medium.

EXAMPLE 2

Foreskin fibroblast cells are grown in 75 cm flasks is a rich culture medium of Medium 199, Earle's salts plus Fetal Calf Serum (FCS). As the cell line expands after serial passings, the cells are inoculated into roller bottles on a roller apparatus using this medium. After confluence of the cells is attained the serum medium is drained and discarded. A serum free medium wherein FCS is omitted is added to the cells and thereafter only serum free medium is used when the cultures are fed. After 1 week of incubation with the serum free medium (i.e., no FCS), the medium is harvested for processing, adding fresh serum free medium to the cultures for future harvest. At this juncture in the life of these cells there is very little growth, i.e., mitotic divisions. The cells produce fibroconectin and procollagen (PROFIPEL). The cells were prepared for storage as noted in Example 1 and were frozen for future use.

The following examples show how I extracted and purified the PROFIPEL molecules from the medium. Of course, my invention is not to be limited to these exemplifications and I contemplate the use of any known purification and separation method.

EXAMPLE 3

Two hundred and fifty mls of the frozen spent medium 1 of Example 1 was thawed overnight in a cold room. The medium was centrifuged in a refrigerated centrifuge in six 50 cc centrifuge tubes, at 15,000 rpm. for 30 minutes.

The clarified medium was added to the top of a Sephadex gel G-150 chromatography column and the filtrate was collected in 20 cc fraction collector test tubes, with approximately 15 mls of fraction per tube. Tubes were monitored on a Beckman Spectrophotometer, OD. 280, for the first appearance of protein. For the column used this occurred at approximately 700 mls. The PROFIPEL molecules, only, are contained in the fractions between 700 and 1000 mls (end of the void volume). The fractions collected from this 300 mls containing the PROFIPEL were pooled.

The 300 mls of collected soluble PROFIPEL were divided into thirty 20 cc lyophilizing ampules with 10 mls of the solute added to each ampule.

The ampules were quickly frozen by placing them into a dry ice-acetone mixture. Ten ampules of the frozen PROFIPEL were then placed into a 1200 cc lyophilizing flask and immediately put onto a large vacuum lyophilizing apparatus at $-55°$ C. This is repeated for ten more ampules until all ampules of PROFIPEL have been lyophilized. The freeze-drying process takes almost 48 hours. Each 20 cc ampule containing 10 mls of soluble PROFIPEL was freeze-dried to about 1.5 mg of solid PROFIPEL. The PROFIPEL was analyzed by gel electrophoresis and showed a complex of fibronectin and procollagen.

The ampules were sealed using a sterile glass seal flaming. The ampules were then stored in a freezer until needed for administration.

EXAMPLE 4

One liter of the frozen spent medium 3 was thawed overnight in a cold room. The spent medium was centrifuged in a refrigerated centrifuge. One liter of the clarified medium is added to the top of a chromatography column containing 5 liters of Sephadex gel G-150.

The fractions from the void volume were collected and pooled. The remaining fractions were discarded. The collected soluble PROFIPEL was divided into 20 cc lyophilizing ampules with 10 mls of the solute added to each capsule.

The ampules were quickly frozen by placing them into a dry ice-acetone mixture. Ten ampules of the frozen PROFIPEL were then placed into a 1200 cc lyophilizing flask and immediately put onto a large vacuum lyophilizing apparatus at $-55\%$C. This is repeated for ten more ampules until all ampules of PROFIPEL have been lyophilized. The freeze-drying process takes almost 48 hours. Each 20 cc ampule containing 10 mls of soluble PROFIPEL was freeze-dried to about 1.5 mg of solid PROFIPEL. The PROFIPEL was analyzed by gel electrophoresis and showed 2 major bands of fibronectin and procollagen I and 1 minor band of procollagen III.

EXAMPLE 5

From the root of an impacted wisdom tooth the remnants of the periodontal membrane were collected and placed in a culture flask containing trypsin. The trypsinite cells (periodontal fibroblast cells) were placed into a small culture flask with Medium 199, Earle's salts, and 10% FCS and incubated at 37° C. with a 5% carbon dioxide atmosphere.

The cells reached confluence in 14 days. These were trypsinized and added to a larger flask. Confluence was reached in seven days thereafter. The cells were trypsinized and added to 3 75 mm culture flasks. The cell line was expanded after serial passings and then the cells are inoculated into roller bottles on a roller apparatus using this medium. After confluence of the cells is attained the serum medium is drained and discarded. A serum free medium wherein FCS is omitted is added to the cells and thereafter only serum free medium is used when the cultures are fed. After 1 week of incubation with the serum free medium (i.e., no FCS), the medium is harvested for processing, adding fresh serum free medium to the cultures for future harvest. At this juncture in the life of these cells there is very little growth, i.e., mitotic divisions. The cells produce fibroconectin and procollagen (PROFIPEL). The cells were prepared for storage as noted in Example 1 and were frozen for future use.

When administered, ampules are opened and a necessary amount of sterile buffered saline for the selected dose is added to the soluble PROFIPEL. It is now ready for injection. A preferred dosage is 0.1 to 5.0 mg per kilogram of body weight of the person or animal being treated. The dosage is to be administered once a week and preferably 3 times a week or even more frequently depending on the severity of the diseased tissue, i.e., once a day.

PROFIPEL can be combined in a gel for topical application, used as an enema, or used in a mist for inhalation therapy.

The compositions of this invention are useful in inhibiting the growth of epithelial tissue diseases caused by a degenerative disease which causes the generation of dedifferentiating cells. In carrying out my novel control method using the compositions of this invention, PROFIPEL, is dissolved in a suitable pharmaceutical carrier, and the solution is injected into the diseased or dedifferentiating cells. In other applications, the PROFIPEL may be put into a salve for topical application, used as an enema or used in a mist for inhalation therapy. The injections are repeated on a regular basis. This inhibits the growth of dedifferentiated cells in the epithelial tissue and thus reduces or slows the growth of the diseased area.

Experiments designed to show the activity of PROFIPEL in suppressing the growth of diseased cells is demonstrated by the following in which, for illustration purposes only, mice were used as exemplary mammals. The determination was carried out as follows:

EXAMPLE 6

The following was done on my behalf by the Sloan Kettering Institute of Cancer Research, Rye, N.Y.

S 180 Tumors were induced in mice by placing S180 mouse sarcoma tumor cells interperitoneally into twenty-one susceptible mice. The PROFIPEL used to treat the mice in Table I, was prepared according to the example 3. The mice treated with the PROFIPEL of Example 3 (two groups) were injected interperitoneally for six days at dosage levels of 50 mg/kg PROFIPEL, and 10 mg/kg, each in 1 ml saline. The control group was given 1 ml sterile saline i.p. The results are given in Table I. In the table, column 1 gives the route of administration, column 2 gives the dose employed, column 3 shows the number of days the mice were treated with PROFIPEL, column 4 indicates the change in animal weight in grams; column 5 shows the number of days the mice survived; column 6 sets forth the medium survival time; column 7 gives the percentage increase in the life span; and column 8 gives the results as being positive or negative.

TABLE I

| Route | PROFIPEL Dose MG/KG/DAY | Therapy (DAY) | Day 7 AWC (9) | Survival DAYS | MST | % ILS | Result |
|---|---|---|---|---|---|---|---|
| ip | 0 | 1-6 | +5.3 | 10,10,11, 11,12,12 12,13,14 14,15 | 12 | | |
| ip | 50 | " | 0 | 13,16,18, 19,19 | 18 | 50 | + |
| ip | 10 | " | +0.2 | 8,13,16, 17,17 | 16 | 33 | + |

The tests showed that the PROFIPEL complex increased the life span (ILS) as much as 50% in the treatment of S180 tumors at a 50 MG per kilogram level, and as much as 33% at a 10 mg per kilogram level.

EXAMPLE 7

The following was done on my behalf by Roswell Park Memorial Institute, Buffalo, N.Y. using the PROFIPEL.

Human renal adenocarcinoma was induced into 12 mice. Six mice were used as a control group and six mice were treated with the PROFIPEL prepared according to Example 1. The PROFIPEL was administered intravenously at 50 mg/kg three times a week— Monday, Wednesday, and Friday. The results are set forth in Table 2.

TABLE II

|  | Days of Survival | Average Survival Days | Tumor Wt. (gms) | Av. Tumor Wt. (gms). |
|---|---|---|---|---|
| Control | 35,28,22 22,25,28 | 26.6 | 4.5,3.7,3.2 5.2,2.8,2.5 | 3.65 |
| PROFIPEL at 50 mg/kg | 4.2,39,35 35,25,42 | 36.0 | 5.8,4.1,3.9 2.3,3.0,5.9 | 4.16 |

The above results tend to show that the PROFIPEL complex interfered with tumor growth since the tumor weights in the treated mice are not much greater than in the control mice over a larger period of time. The treated mice had a substantial increase in their life span.

The advantages of using the PROFIPEL complex should be apparent. Since the PROFIPEL is synthesized from human mesenchymal tissue, it is not using foreign bodies, will not cause immunological breakdown or damage to healthy tissue, and further, the PROFIPEL promotes the redifferentiation of diseased cells and tissue in degenerative diseases.

Those who are skilled in the art will readily perceive how to modify the invention. Therefore, the appended claims are to be construed to cover all equivalents within the true scope and spirit of the invention.

I claim:

1. A method of treating chronic degenerative diseases of the tissue comprising treating the diseased tissue with a pharmaceutical complex of macromolecules wherein said macromolecules are derived from the culture media of cells selected from the group consisting of animal and human mesenchymal cells and wherein the complex of macromolecules comprises both fibronectins and procollagens.

2. The method of claim 1 wherein the macromolecules further include proteoglycans.

3. The method of claim 1 wherein the macromolecules further include macromolecules selected from the group consisting of proteoglycans, laminins, elastins and mixtures thereof.

4. The method of claim 1 wherein the macromolecules in the complex have the same quantitative relationthip as those in the mesenchymal cells from which they were extracted.

5. The method of claim 3 wherein the macromolecules in the complex have the same quantitative relationship as those in the mesenchymal cells from which they were extracted.

* * * * *